US009392966B2

(12) United States Patent
Ten Kate

(10) Patent No.: US 9,392,966 B2
(45) Date of Patent: Jul. 19, 2016

(54) FALL PREVENTION SYSTEM

(75) Inventor: Warner Rudolph Theophile Ten Kate, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1118 days.

(21) Appl. No.: 13/060,440

(22) PCT Filed: Aug. 27, 2009

(86) PCT No.: PCT/IB2009/053752
§ 371 (c)(1),
(2), (4) Date: Feb. 24, 2011

(87) PCT Pub. No.: WO2010/026513
PCT Pub. Date: Mar. 11, 2010

(65) Prior Publication Data
US 2011/0152727 A1 Jun. 23, 2011

(30) Foreign Application Priority Data
Sep. 4, 2008 (EP) .................................... 08163681

(51) Int. Cl.
*A61B 5/103* (2006.01)
*A61B 5/117* (2006.01)
*A61B 5/11* (2006.01)
(Continued)

(52) U.S. Cl.
CPC ............. *A61B 5/1117* (2013.01); *A61B 5/6828* (2013.01); *A61B 5/6829* (2013.01); *A61B 5/6831* (2013.01); *G08B 21/0446* (2013.01); *A61B 5/1038* (2013.01); *A61B 5/112* (2013.01); *A61B 2562/0219* (2013.01); *A63B 24/00* (2013.01); *A63B 24/0003* (2013.01); *A63B 24/0006* (2013.01)

(58) Field of Classification Search
CPC .. A61B 5/6828; A61B 5/1117; A61B 5/6829; A61B 5/1038; A61B 5/112; A63B 24/00; A63B 24/0003; A63B 24/0006
USPC .......... 600/595, 587; 700/93; 702/153; 428/8
See application file for complete search history.

(56) References Cited

U.S. PATENT DOCUMENTS 6,895,341 B2 * 5/2005 Barrey et al. .................... 702/32
7,988,647 B2 * 8/2011 Bunn et al. ..................... 600/595
(Continued)

FOREIGN PATENT DOCUMENTS

JP H03166076 A 7/1991
JP 2001277158 A 10/2001
(Continued)

OTHER PUBLICATIONS

Saltzman, Elliot; Kelso, J. A. "Skilled actions: A task-dynamic approach". Psychological Review, vol. 94(1), Jan. 1987, 84-106.*
(Continued)

*Primary Examiner* — Devin Henson

(57) ABSTRACT

There is provided a system for fall prevention for a user, comprising one or more sensors for attachment to respective portions of the body, each sensor being adapted to measure movement of the respective portion of the body and to translate the movement into a signal; and a controller adapted to receive the signal or signals and to determine a risk of falling by estimating a trajectory of the center of mass of the user relative to a trajectory of a lower portion of the body from the signal or signals.

18 Claims, 5 Drawing Sheets

(51) Int. Cl.
   *A61B 5/00* (2006.01)
   *G08B 21/04* (2006.01)
   *A63B 24/00* (2006.01)

(56) References Cited

U.S. PATENT DOCUMENTS

| | | | |
|---|---|---|---|
| 8,460,219 B2* | 6/2013 | Miyake | 600/595 |
| 2005/0021312 A1 | 1/2005 | Tanaka et al. | |
| 2006/0195050 A1* | 8/2006 | Alwan et al. | 600/595 |
| 2006/0270950 A1* | 11/2006 | Dariush | 601/5 |
| 2007/0054777 A1 | 3/2007 | Kawai et al. | |
| 2007/0073196 A1* | 3/2007 | Tanaka et al. | 600/595 |
| 2008/0045804 A1* | 2/2008 | Williams | 600/300 |
| 2008/0108913 A1* | 5/2008 | Lengsfeld et al. | 600/595 |
| 2009/0079559 A1* | 3/2009 | Dishongh et al. | 340/539.13 |
| 2009/0254003 A1* | 10/2009 | Buckman | 600/595 |
| 2009/0260426 A1* | 10/2009 | Lieberman et al. | 73/65.01 |
| 2010/0049096 A1* | 2/2010 | Ten Kate | 600/595 |
| 2010/0124737 A1* | 5/2010 | Panzer | 434/308 |
| 2011/0126731 A1* | 6/2011 | Vacher et al. | 104/31 |
| 2011/0166488 A1* | 7/2011 | Miyake | 601/34 |
| 2011/0214941 A1* | 9/2011 | Petty et al. | 182/9 |
| 2011/0312473 A1* | 12/2011 | Chu et al. | 482/54 |
| 2012/0095722 A1* | 4/2012 | Ten Kate | 702/141 |
| 2013/0000156 A1* | 1/2013 | Andoh | 36/136 |
| 2013/0182884 A1* | 7/2013 | Mitsuhashi | 381/395 |
| 2013/0228394 A1* | 9/2013 | Sousa et al. | 182/3 |
| 2013/0246088 A1* | 9/2013 | Huster et al. | 705/2 |
| 2013/0283696 A1* | 10/2013 | Zhang | 49/322 |

FOREIGN PATENT DOCUMENTS

| | | |
|---|---|---|
| JP | 2004252618 A | 9/2004 |
| JP | 2005237504 A | 9/2005 |
| JP | 200861811 A | 3/2008 |
| WO | 2004014230 A1 | 2/2004 |
| WO | WO 2006038712 A1 * | 4/2006 |
| WO | WO2008059418 | 5/2008 |

OTHER PUBLICATIONS

Samer S. Hasan et al. "Simultaneous measurement of body center of pressure and center of gravity during upright stance. Part I: Methods" Gait & Posture, vol. 4, Issue 1, Jan. 1996, pp. 1-10.*

McGibbon et al., "Ligament and Tendon Loads from Gait Data", Gait & Posture, 1994; 2: No. 1.

Villanueva et al., "Method for Monitoring Acceleration of the Trunk During Gait", Proceedings of the Second Joint EMBS/BMES Conference, Houston, TX USA, Oct. 23-26, 2002, pp. 1758-1759.

Hernandez et al., "Changes in Distal Postural Control Accuracy Near the Limits of the Base of Support", Dept. of Biomedical Engineering, Institute of Gerontology, Biomechanics Research Laboratory, Mobility Research Center, Division of Geriatric Medicine, Department of Internal Medicine, the University of Michigan, VA Ann Arbor Health Care System Geriatric Research, Education and Clinical Center, Ann Arbor, Michigan.

Rogers et al., "Lateral Stability During Forward-Induced Stepping for Dynamic Balance Recovery in Young and Older Adults", The Journals of Gerontology Series A: Biological Sciences and Medical Sciences 56:M589-M549 (2001).

Krebs et al., "Is Base of Support Greater in Unsteady Gait?", Physical Therapy, vol. 82, No. 2, Feb. 2002, pp. 138-147.

Patton et al., "A Simple Model of Stability Limits Applied to Sidestepping in Young, Elderly and Elderly Fallers", Proceedings of the 28th IEEE, EMBS Annual International Conference, New York City, USA, Aug. 30-Sep. 3, 2006, pp. 3305-3308.

Dingwell et al., "Nonlinear Time Series Analysis of Normal and Pathological Human Walking", CHAOS, vol. 10, No. 4, Dec. 2000, pp. 848-863.

Zijlstra et al., "Assessment of Spatio-Temporal Gait Parameters from Trunk Accelerations During Human Walking", Gait & Posture 18 (2003), Institute of Human Movement Sciences, University of Groningen, the Netherlands, pp. 1-10.

Han et al., "Estimation of the Center of Body Mass During Forward Stepping Using Body Acceleration", Proceedings of the 28th IEEE EMBS Annual International Conference, New York City, USA, Aug. 30-Sep. 3, 2006, pp. 4564-4567.

Rogers et al: "Control of Frontal Plane Body Motion During Induced Forward Stepping"; North American Congress on Biomechanics, Nacob 98, pp. 1-3.

Jian et al: "Trajectory of the Body COG and COP During Initiation and Termination of Gait"; Gait 7 Posture 1993, 1:9-22.

Hof et al: "The Condition for Dynamic Stability"; Journal of Biomechanics, 38 (2005), pp. 1-8.

Agiovlasitis: "Three-Dimensional Motion of the Center of Mass and Energeetic Cost Across a Variety of Walking Speeds: A Comparison Between Adults With and Without Down Syndrome"; Dissertation Submitted to Oregon State University, 2007, 110 Page Document.

Dhaher et al: "Postural Balance Modeled as a Double Inverted Pendulum"; Gait & Posture 1994, 2:No. 1, p. 56.

* cited by examiner

FALL PREVENTION SYSTEM

TECHNICAL FIELD OF THE INVENTION

The invention relates to a fall prevention system, and in particular to a fall prevention system that monitors the centre of mass of a user relative to a lower portion of the user's body.

BACKGROUND TO THE INVENTION

Falls affect millions of people each year and result in significant injuries, particularly in the elderly. In fact, it has been estimated that falls are one of the top three causes of death in elderly people.

A fall is defined as a sudden, uncontrolled and unintentional downward displacement of the body to the ground. There are currently some fall detection systems available that detect these falls and allow the user to obtain assistance manually or automatically if a fall occurs. Exemplary fall detection systems can comprise personal help buttons (PHBs) or worn and/or environment-based automatic detection systems.

Automatic fall detection systems comprise one or a set of sensors that continuously measure the movement of the user, and a processor that compares the measured or processed signals with predetermined thresholds in order to detect a fall. In particular, automatic fall detection systems store a set of predetermined threshold values and/or classification patterns (which are hereinafter referred to as parameter sets). When the system is activated, movement data obtained from the sensors (such as, for example, an accelerometer) will be continuously transformed and processed, and then compared with those parameter sets to determine if a fall event occurs.

Many fall detection systems also calculate a change in the orientation of the fall detection system (and hence the user) and detect an impact with the ground during a fall event.

A disadvantage of these systems is that they lack full reliability. Furthermore, they do not actually prevent falling, but provide a warning or alarm in the event that a user already has fallen.

However, users that are insecure during walking, for example caused or enhanced by a fear of falling or by fatigue in the muscles or that are frequently multi-tasking, i.e. they are carrying items when walking, talking to their grandchild, etc, or that move in places where there is dim lighting, a wet or irregular ground surface (such as loose carpet, electricity wires, toys, tools, and other hazards) or that are under medication that may affect balance or concentration can be assisted by a system for fall prevention, which decreases the actual risk of falling or at least helps them to avoid situations where there is a higher risk of falling, and makes them feel more safe.

WO 2008/059418 describes a system for fall prevention for a user, comprising a number of sensors attachable to at least one lower body segment, in which the sensors are adapted to measure movement of the at least one lower body segment and to translate the movement into a signal, the system further comprising a control adapted to receive the signal from the respective sensors, observe the signal as an actual sequence of postures of the at least one lower body segment, compare the actual sequence with a predetermined sequence of postures as a function of time (the predetermined sequence relating to a low risk of falling), and to determine a high risk of falling when the actual sequence deviates from the predetermined sequence (to a certain degree).

Thus, this system provides a way of indicating when falls are more likely to occur, with the increased risk occurring when there is a variation in the trajectory of the feet of the user.

It is an object of the invention to provide a system for fall prevention that improves on that described above.

SUMMARY OF THE INVENTION

Fall prevention systems can be based on detecting a temporary increase in the risk of falling, which will be observable as a decrease in the stability or other parameter in the gait of the user. Thus, the invention provides a fall prevention system that is based on monitoring the trajectory of the centre of mass (CoM) of the user's body relative to a lower portion of the user's body.

Therefore, while in the prior art system a larger variation or deviation in the trajectory of the feet leads to the detection of an increased risk, the invention provides that this only leads to the detection of an increased risk if at the same time the centre of mass of the user's body is also varying significantly. Thus, the invention is able to distinguish changes in gait that may be caused by an irregular surface (which increases the variation in the base of support but not necessarily the variation of the centre of mass). Conversely, an increase in the variation of the trajectory of the centre of mass of the user's body only leads to the detection of an increased risk in the invention if there is not a corresponding increase in the base of support.

In accordance with a first aspect of the invention, there is provided a system for fall prevention for a user, comprising one or more sensors for attachment to respective portions of the body, each sensor being adapted to measure movement of the respective portion of the body and to translate the movement into a signal; and a controller adapted to receive the signal or signals and to determine a risk of falling by estimating a trajectory of the centre of mass of the user relative to a trajectory of a lower portion of the body from the signal or signals.

In some embodiments of the invention, the controller determines the risk of falling by directly estimating the trajectory of the centre of mass of the user relative to the trajectory of the lower portion of the body (for example directly estimating a difference between the two trajectories). In alternative embodiments, the controller determines the risk of falling by separately estimating the two trajectories and then comparing them.

In accordance with a second aspect of the invention, there is provided a method of prevention of falls by a user, the method comprising attaching one or more sensors to respective portions of the user's body; each sensor measuring the movement of the respective portion of the body and translating the movement into a signal; and determining a risk of falling by estimating a trajectory of the centre of mass of the user relative to a trajectory of a lower portion of the body from the signal or signals.

In accordance with a third aspect of the invention, there is provided a computer program product, comprising computer code that, when executed on a computer or processor, performs the steps of receiving a signal or signals from one or more sensors attached to respective portions of a user's body, each sensor measuring the movement of the respective portion of the body and translating the movement into a signal; and determining a risk of falling by estimating a trajectory of the centre of mass of the user relative to a trajectory of a lower portion of the body from the signal or signals.

BRIEF DESCRIPTION OF THE DRAWINGS

The invention will now be described, by way of example only, with reference to the following drawings, in which.

DETAILED DESCRIPTION OF THE PREFERRED EMBODIMENTS

As described above, the invention provides a system for fall prevention that detects a temporary increase in the risk of falling based on monitoring the trajectory of the centre of mass (CoM) of the user's body relative to a lower portion of the user's body.

In the following, "trajectory" is to be understood as referring to the path followed by the relevant portion through space represented as a sequence of positions. Since a (temporary) risk of falling is derived from some distance measure related to the trajectory, the velocity is to be understood to be included in "trajectory", so as to correct for the effect velocity may have, if any, on the chosen distance measure. For example, if the centre of mass is tested for moving within a certain area, it may move physically outside that area, provided that it is accompanied by a velocity that will conduct it inwards. Its "trajectory" is inside the area (although the distance measure might be estimated to be beyond critical). Vice versa, a centre of mass that moves physically within the area but exhibits a strong velocity outwards might be estimated as being on a trajectory outside the area. These corrections are clear for those skilled in the art.

The centre of mass (CoM) of the user's body and base of support (BoS) are concepts known in the art, together with the centre of pressure (CoP). They are used to model the way a human maintains balance while standing. The centre of mass is a mechanical quantity that defines the point that can represent the translational movement of the whole body. It is also the point around which the body would rotate in free space. For a human body, the CoM is located near the pelvis. Thus, a sensor for estimating the trajectory of the CoM is preferably attached close to the pelvis.

The base of support (BoS) is defined for standing, i.e. for a static situation, and is roughly the area covered by a quadrilateral shape that surrounds both feet.

Figure 1:
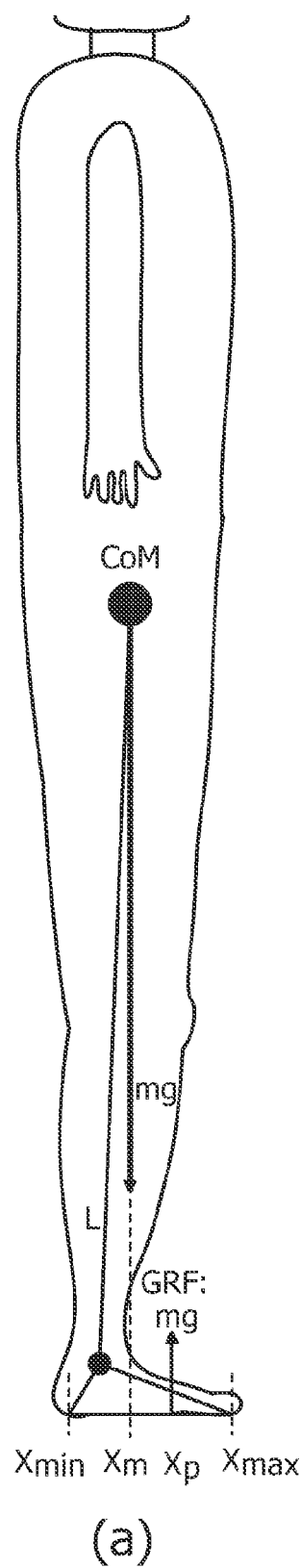
FIGS. 1(a), 1(b) and 1(c) illustrate the concepts of centre of mass, base of support and dynamic base of support.
Figure 1:
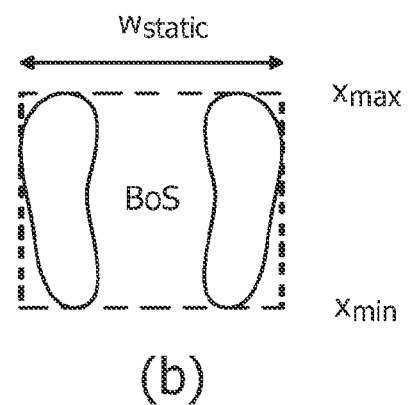
Figure 1:
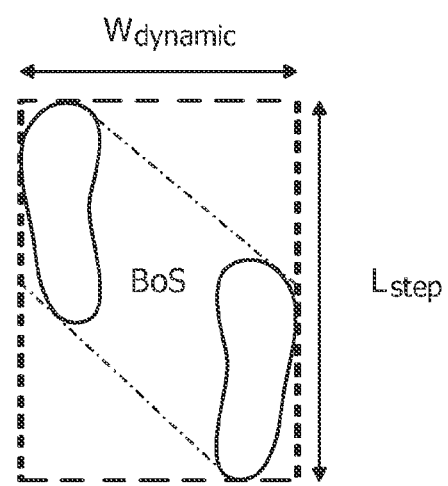

A person that is standing is stable if the centre of mass stays within the base of support. The person maintains this stability by changing the point of pressure on the ground. This introduces the notion of the centre of pressure (CoP). Usually, an upright standing person is modeled as an inverted pendulum, where the ankles represent the hinges. Gravity, attached at the CoM, and ground reaction forces (GRF), attached at the CoP, create moments of force around these hinges, causing the person to sway back and forth. These concepts are illustrated in FIGS. 1(a) and 1(b). If the moment of the GRF cannot compensate the moment of gravity, then the person will fall. This almost certainly happens if the CoM ($x_m$) extends outside the BoS (and the person does not displace a leg—which is the assumption for a standing posture).

The base of support of a person when they are walking is not so clearly defined. For the purposes of this invention, the dynamic base of support (i.e. the base of support during movement, such as walking) is defined as the surface spanned by the step width ($W_{dynamic}$) and step size ($L_{step}$), as shown in FIG. 1(c).

Thus, the invention is based on the realization that variation or deviation is a necessary measure for falling, but is not guaranteed on its own to be a sufficient measure for determining a fall risk. The variation or deviation provides information about the stability of the movement itself, i.e. the stability of the movement pattern. The invention accounts for the stability of movement in terms of its capability to recover from potential perturbations, i.e. how much margin is left from the "point-of-no-return" where the centre of mass moves outside the base of support. When measuring the average risk of falling, the variation in gait is sufficient to estimate the risk, since a constant BoS can be assumed. However, when measuring the dynamic risk, however, the assumption isn't always satisfied and it is necessary to measure the trajectory of the centre of mass relative to the base of support.

Thus, the dynamic risk of falling is determined by estimating the step size ($L_{step}$) and step width ($W_{dynamic}$) for each step, which are considered together to give the instantaneous BoS, determining the trajectory traversed by the centre of mass during that step (or the surface area traversed by the CoM formed from a two-dimensional extension of the trajectory which includes a forward and sideways movement relative to the face/movement direction of the person; and that gives a surface if a rectangle is drawn around the trajectory made in one step), and determining the risk of falling from the dynamic distance between the CoM and BoS trajectories, in particular from the minimum of |CoM-BoS|. Since the position cannot be measured in absolute coordinates, it is assumed in a simple implementation that the centre of both the BoS and CoM align. However, more sophisticated algorithms can be used to refine this estimation.

The location of the boundaries of both the CoM and BoS are compared for:

(i) whether the BoS contains the CoM; and (ii) the margin or distance from the CoM boundary to the BoS boundary.

For point (i), the CoM can be occasionally found outside the BoS during walking, but this does indicate a high risk of falling. For point (ii), a small margin is interpreted as presenting an increased risk for falling, where "small" is relative to the usual margin for that user.

When an increased risk is found, the user can be warned to be more alert, or to have a rest, e.g. sit for a while. The risk episodes can also be accumulated and be provided to the care giver, who can use the information for further advice or treatment of the user.

Figure 2:
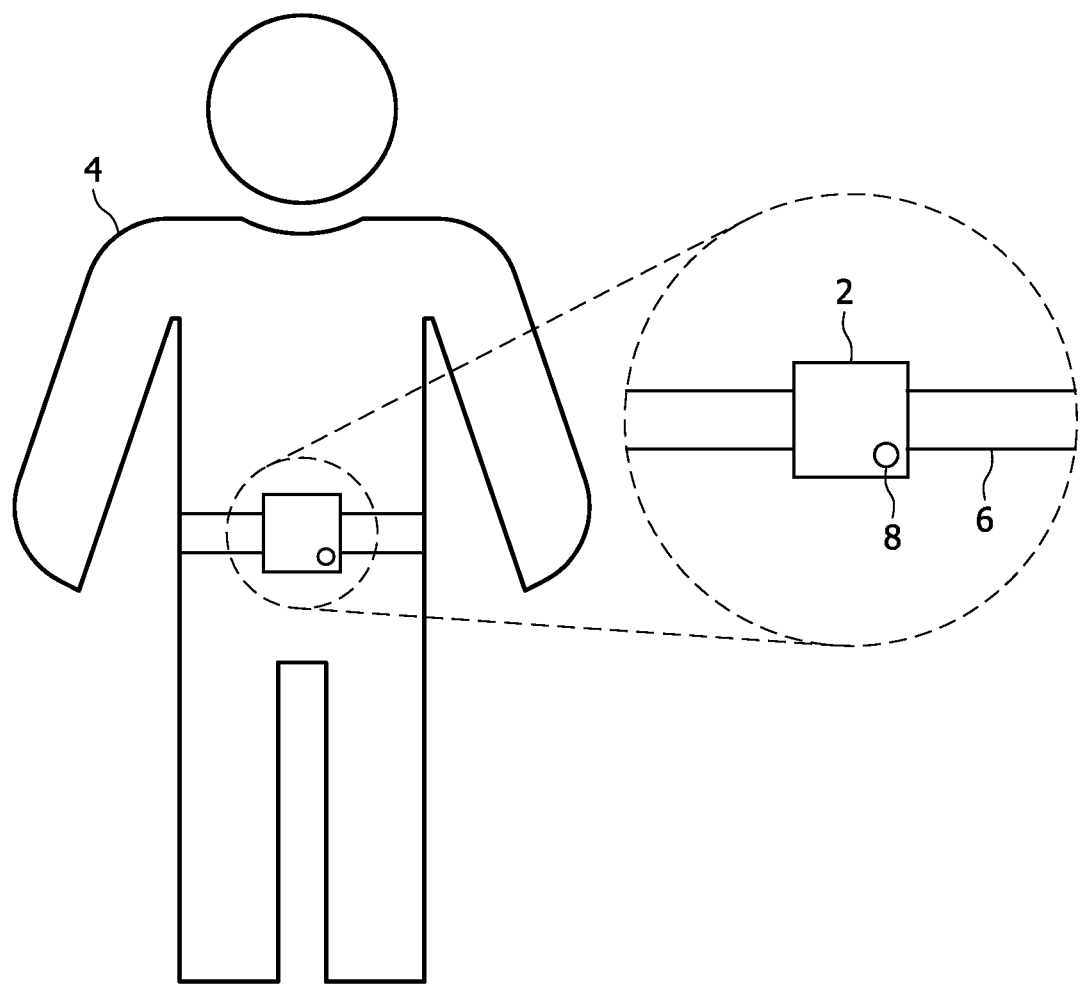
FIG. 2 shows a fall prevention system in accordance with a first embodiment of the invention.

FIG. 2 shows a system for fall prevention 1 in accordance with a first embodiment of the invention attached to a user 4 via a band or other attachment means 6. In this embodiment, the system 1 comprises a single unit 2, which is preferably attached to a part of the user's body such that the sensor in the unit 2 can measure the periodicity of the walking patterns. Thus, the unit 2 can be attached at the trunk or an upper part of the user's body 4, such as around the head. At lower positions (such as on the legs), the walking signal (i.e. the accelerations induced by walking) will be stronger. For example, at the feet, only gravity will be observed during the stance phase of that foot, allowing the velocity to be set to zero without the need for it to be estimated from other means. However, when the unit 2 is attached to upper parts, the periodicity of the walking signal will be doubled, because both legs contribute comparably to the signal wave forms (the upper part will register accelerations when each foot hits the ground).

In this embodiment, the unit 2 includes a button 8 that the user 4 can operate to send an alarm signal to a call-centre or other assistance unit if they fall and require assistance.

Figure 3:
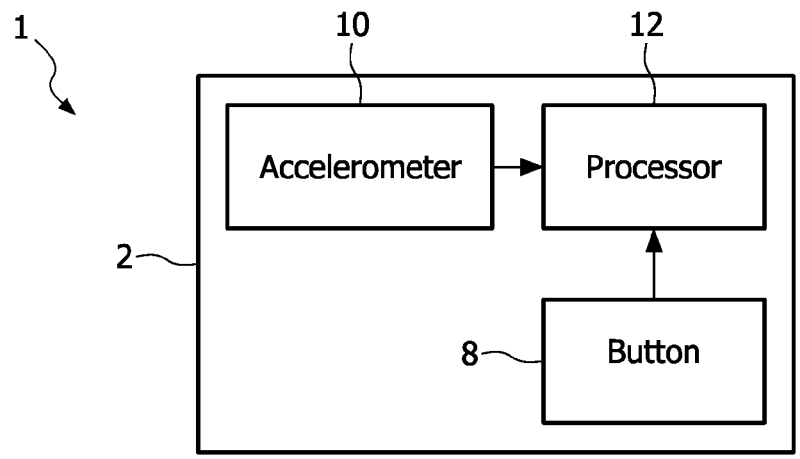
FIG. 3 shows a block diagram of the fall prevention system of FIG. 2.

FIG. 3 shows the unit 2 of the system 1 in more detail. The unit 2 comprises one or more sensors 10 for monitoring the movement of the user 4, and a processor 12 for analyzing the signals from the sensors 10 to determine whether the user 4 is at an increased risk of falling, is about to fall, or whether the user 4 has fallen. The sensors 10 typically include an accelerometer for measuring the acceleration experienced by the system 1.

The one or more sensors 10 can include sensors in addition to the accelerometer, for example gyroscopes (for determining the orientation of the unit 2), air-pressure sensors (for helping to determine whether a change in height of the unit 2 when the user falls), in-sole pressure sensors (when the unit 2 is to be placed on a foot), electromyography (EMG) sensors, magnetometers (for measuring changes in the orientation of the unit 2 relative to the Earth's magnetic field) and temperature sensors.

Other sensors to assist in the estimation of the position can be included. Position can be estimated from a double integration of the accelerometer signals, expressed in the global coordinate system. This integration needs boundary conditions for velocity and position. Since each step is measured, the starting position can be arbitrarily chosen to be zero for each step. As mentioned above, when measured at the feet, the starting velocity is known to be zero during the stance phase. At the other measurement locations, an estimate is to be made, which, for example, can be derived from the measured step size at the feet and the stepping time, by using an inverted pendulum model (for example as described Zijlstra & Hof, Gait & Posture 18 (2003) 1-10), possibly with a requirement that the average sideways velocity is zero.

In this embodiment, the variation of the walking pattern is observed. This can be the traditional variation as defined in statistics, but can also be a non-linear measure, such as the maximal Lyapunov exponent or Floquet Multiplier (for example as described in "Nonlinear time series analysis of normal and pathological human walking" by J. B. Dingwell et al, Chaos 10(4), 2000, 848-863). These measures indicate how stable the pattern itself is. In this embodiment, it is assumed that the BoS doesn't vary much, so a large deviation in the CoM will indicate an increased risk of falling.

Figure 4:
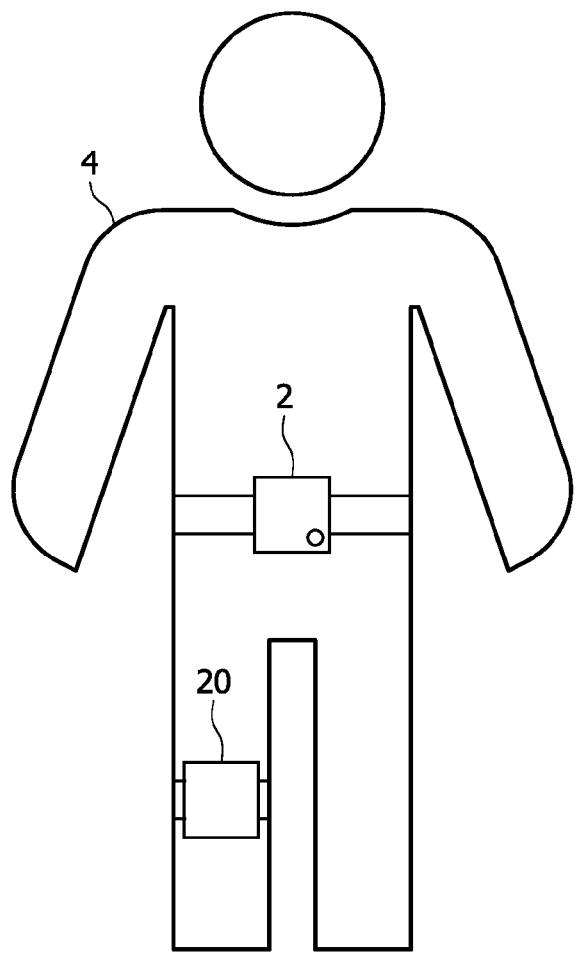
FIG. 4 shows a fall prevention system in accordance with a second embodiment of the invention.

FIG. 4 shows a second, more preferred embodiment of the invention. In this embodiment, the system 1 comprises a unit 2 as before, which is now preferably attached at or near the centre of mass of the user 4 (although it can be attached to the head or upper torso of the user 4), which means that the accelerometer 10 in the unit 2 can measure the accelerations acting on the centre of mass of the user 4. In this embodiment, the system 1 further comprises a second unit 20 that is preferably for attachment to a leg, ankle, foot, heel or toe of the user 4, perhaps via a band or other attachment means, or the unit 20 can be incorporated into a sock or shoe for the user to wear, for example as part of the shoe or as an in-sole. The second unit 20 includes a respective accelerometer, so that it can measure the accelerations experienced by the leg or foot. The second unit 20 may also include other sensors as described above with respect to the first embodiment.

Thus, in this two-sensor embodiment, the sensor attached close to the pelvis measures the movement of the CoM, and the sensor attached to a foot (for example in a shoe), measures the dynamic BoS.

In this embodiment, it is assumed that the gait of the user 4 has perfect anti-phase symmetry, which means that if, say, the sensor is attached to the left foot, then the signal for the right foot is estimated to be the symmetric counterpart of the measured signal from the left foot (i.e. it is mirrored in the lateral direction, but identical in the sagittal direction), time shifted by half a period.

If it is known that the user 4 has an asymmetric gait, for example, from a clinical observation, the left-right transposition can be adapted accordingly.

Figure 5:
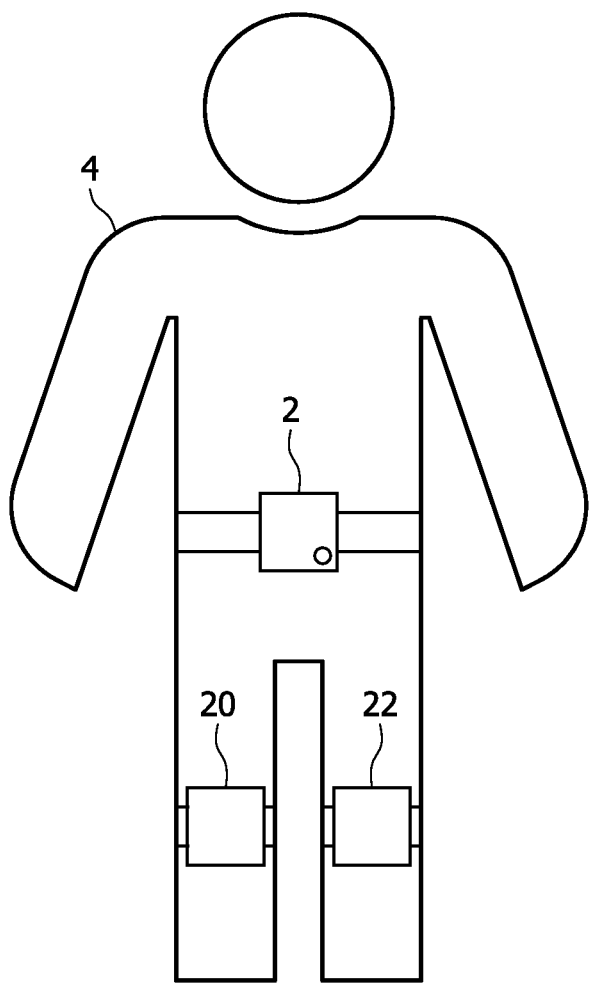
FIG. 5 shows a fall prevention system in accordance with a third embodiment of the invention.

FIG. 5 shows a third, even more preferred, embodiment of the invention. In this embodiment, there is a third unit 22 that is provided for attachment to the other leg or foot of the user 4, again via a band or other attachment means, or incorporated into a sock or shoe.

It will be appreciated that the embodiments above are "preferred" from the point of view of being able to provide a reliable identification of when a user is at an increased risk of falling, rather than for the comfort of the user (who generally prefers as few sensors and units as possible).

Figure 6:
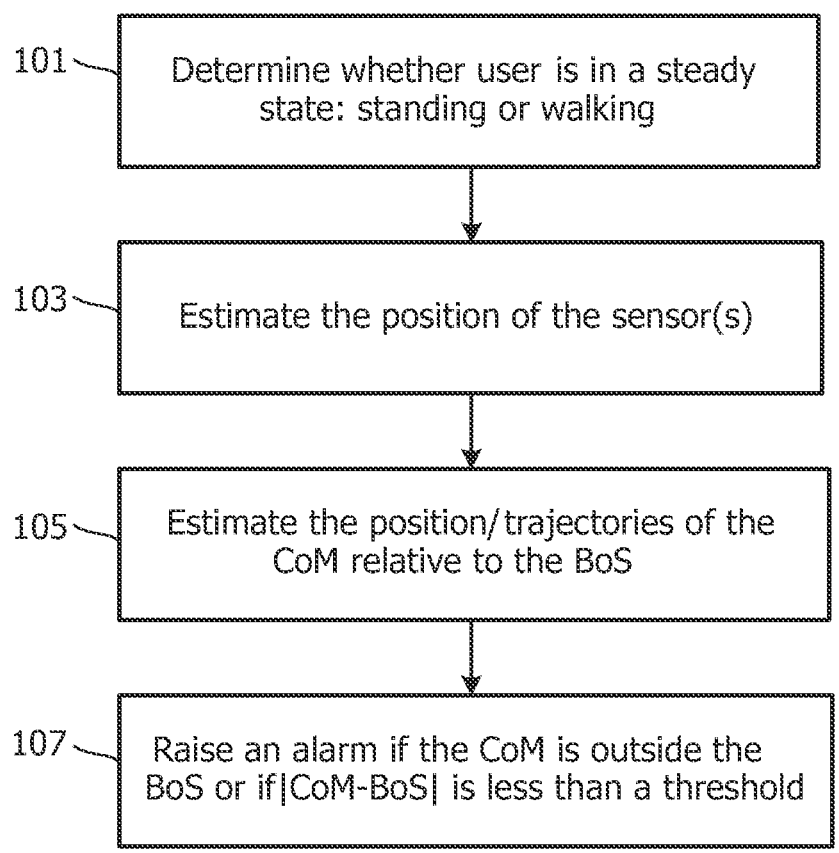
FIG. 6 shows a method in accordance with the invention.

The processor 12 of the unit 2 processes the signals from the sensor(s) as described below and shown in FIG. 6.

Firstly, the processor 12 detects whether the person is in a steady state: standing or walking (step 101). For a steady state in standing, the signal has to vary around some mean value. For a steady state in walking, the signal has to be periodic within reasonable limits. A limit cycle should be detectable (i.e. a recurring pattern when plotting the signal parameters as they develop over time in some multidimensional space). In standing, the foot or feet sensors should be relatively at rest (so no acceleration detected). In embodiments where an air-pressure sensor included in a unit at the CoM position, the sensor's height provides additional support for the posture being upright. Since the person is standing, there is no further estimate of the BoS and only the variation of the CoM is monitored, as in the single sensor solution.

In walking, the periodicity in the steady-state signal is used to delineate the individual cycles (steps). For example, at each heel strike, there will be an increased acceleration, due to the absorption of the residual foot speed. This peak can be used to delineate the step boundary. Usually, at the CoM, the peak is better detectable by observing the norm of the acceleration vector. At the BoS, the peak is better detectable by observing (the norm of) the derivative of the acceleration. If the sensors are not time synchronized, this is done for both sensor signals separately, and this peak can actually be used to synchronize the sensors. Otherwise, the time synchronization is used and the time of heel strike found by the different sensors can be used to refine the cycle delineation. Another approach is to measure vertical displacement and observe the instants where height returns to its reference height. Appropriate compensation for drift and gravity has to be taken.

The second step (step 103) is to estimate the position of the sensors. This is done by performing a double integration of the accelerometer signals, and consequently the result can easily drift due to offset in the accelerometer signal (offset is often present due to gravity together with an incorrect estimate of the sensor's orientation). The drift can be compensated by using the delineated cycle boundaries, as well as the fact the pattern is steady-state. The average vertical velocity is required to be zero, since there is no change in height. The average forward (moving) velocity is required to be constant, since the user is assumed to be walking at a constant pace. This constant isn't known in advance, and may change over time.

The velocity is found by integration of the accelerometer signals, from one cycle boundary to the next. The initial velocity at the first cycle is set to zero (or any other appropriate value). The velocity in the next cycle is estimated by using a low-pass filter over the velocities found in the preceding cycles. For example, by means of a running average filter: after each step, the velocity is updated to the weighted average of the previously used value and the newly found value: $v_{new}=(1-)*v_{old}+\alpha*v_{measured}$. $\alpha$ is typically 0.10. This $v_{new}$ is used as the initial velocity for the integration in the next cycle. Since the velocity can adapt, it cannot be used to compensate the drift in the measured acceleration. Thus, in order to provide a mechanism for compensating the drift, the average acceleration is required to be zero over each step. This is in line with requesting a constant velocity: at constant velocity, the integral of the acceleration vanishes, i.e. the average acceleration is zero.

The position of each sensor (i.e. preferably at the CoM and on both legs or feet) is set to zero at the start of each cycle (each step), so that the step size and step width is the outcome of the full integration. More precisely, the maximum values over the whole step cycle are taken as estimates of the size and width. The (straight-line) trajectories of the CoM and BoS are computed from these positions. At initiation, the centers of the trajectories are aligned with each other. This alignment can be applied at each step again, but it is also possible to allow the centers to adapt using a running average or similar filter.

In an alternative embodiment, instead of the BoS having a particular surface area for a step, it can be assumed to be dynamic during the step itself, i.e. it is at its smallest when the swinging leg passes the stance leg. The CoM has to be inside this BoS all of the time for the user to be stable. In this case, the midpoints of the trajectories of the CoM and BoS must be aligned, and the starting positions cannot be assumed to be equal. It will be appreciated by those skilled in the art that this model is simplified and can be further refined. In particular, the CoM can be temporarily outside the BoS and present a relatively low risk of falling provided that the CoM has sufficient velocity to bring it back into the BoS. Alternatively, if the CoM is within the BoS but has a relatively high velocity "outwards" (i.e. away from the centre of the BoS), the risk of falling can be relatively high. As described above, this velocity effect of the CoM or BoS can be incorporated in the trajectory estimate. It can equally be treated separately.

The integration should be performed in the horizontal plane. Therefore, an estimate has to be made as to what component of the signal from the accelerometer(s) is in the horizontal direction. This in turn requires knowledge about the orientation of the sensor. The orientation can be estimated from the DC component in the sensor, which is due to gravity, or, when available in the fall prevention system 2, from other sensors, such as a magnetometer and/or a gyroscope.

In an alternative embodiment, with respect to the position of the centre of mass, the vertical trajectory of the corresponding sensor can be monitored and translated into a horizontal displacement, for example using an inverted pendulum model.

In the third step (step 105), the processor 12 estimates the position of the centre of mass relative to the base of support. As described above, the base of support is defined to be the step size $L_{step}$ times the step width $W_{dynamic}$. The origins of the CoM and BoS are assumed to be aligned, and they can be adapted through a low-pass-filter.

For the step-width, an additional DC step (offset) width can be assumed, to account for the natural spacing between feet. For example of 20-30 cm. However, in principle, the exact offset width doesn't matter as the system 2 will raise a warning that there is an increased fall risk if it tests for a deviation in the patterns in a relative sense, rather than in an absolute sense.

If the processor determines that the CoM is expanding closely to the BoS, i.e. if both surfaces reach a similar size (so |CoM-BoS| is less than a threshold) or that the CoM is outside the BoS, an alarm is raised to the user (step 107), to warn the user that they are at an increased risk of falling. The alarm can be an audible or visible signal, but alternatively in another form, such as a vibration or other tactile sensation. The occurrence or the rate of occurrences can be communicated with a service provider or care giver.

In further embodiments of the invention, the algorithm executed by the processor 12 to detect an increased risk of falling can be improved by treating the left and right steps separately to refine the step size used in determining the BoS, or by considering the double support phase separately (the double support phase being the period in the gait when both feet are touching the ground). During this phase, the static stability measure, as defined for standing, can be used. In that sense, the risk of falling can be distinguished in two parts: one is estimated during the double support phase, the second during swing.

In further embodiments of the invention, the fall prevention system can be extended such that it can be used with users that have some form of aid for walking, such as a stick or frame. In these embodiments, the BoS is measured as the (dynamic) area spanned by the user's feet and the stick or frame. A unit can be mounted on the stick or frame, instead of to the user. A correction can be applied in the algorithm for the division of the user's body weight over feet and the stick or frame. With a frame, the user will bend forward, which implies a shift in the position of the CoM. Also, since the frame supports force, the position of the CoM will move to another place at the trunk and the preferred attachment position will change.

As described above, other sensors can be used in addition to accelerometers. Gyroscopes can be used to ease the estimate of the sensor's orientation. Magnetometers can be used to complement the DC-directional information indicated by gravity. EMG sensors could be added to observe muscle activity and thus provide a better estimate of the capability to counter perturbations (i.e. the EMG sensor can estimate reaction speed and strength). Fatigue could be observed, which indicates an increased risk of falling. Another measure could be to observe the CoP, for example using pressure sensors in the user's shoes. These pressure sensors could be used to refine the stability estimate by computing countering moments to the movement of the CoP. This can be particularly useful during the double support phase. In-sole (shoe) pressure sensors can also be used to estimate the step boundaries (heel strike and toe off).

In further embodiments of the invention, instead of observing the CoM and BoS separately, the stability of the combined signal |CoM-BoS| could be monitored. This stability can be distance between the CoM and BoS, but alternatively the variation in the distance. Since, physiological processes such as walking exhibit non-linear characteristics, a more sophisticated analysis will result from observing corresponding (non-linear) quantities. In particular, the maximal Lyapunov exponent and Floquet Multipliers are useful quantities. For example, instead of observing the position trajectory of CoM and BoS relative to each other, the maximal Lyapunov exponents measured at CoM and BoS locations are compared. The exponents are directly estimated from the sensor signals, i.e. not requiring the double integration.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for fall prevention for a user, comprising:
one or more sensors configured to be attached to respective portions of the body of a walking user to measure movements of a moving center of mass of the user and a moving base of support of the body and to translate the measured movements into signals, the base of support of the user being a surface defined by a step width and a step length of the user when walking; and
a controller configured to receive the signals and to determine a risk of falling of the walking user by estimating a difference between a trajectory of the moving center of mass of the user relative to a trajectory of the moving base of support of the body from the signals.

2. The system as claimed in claim 1, wherein the controller is further configured to:
determine whether the signals have a reoccurring pattern over time in multi-dimensional space; and
based on periodicity of the reoccurring pattern, determining whether the user is in a walking steady state.

3. The system as claimed in claim 2, wherein the controller is further configured to:
determine periodicity of the signals when the user is in the walking steady state by detecting peaks in at least one of the movement signals to delineate individual steps.

4. The system as claimed in claim 3, wherein the controller is further configured to:
from the signals for each step, determining (1) the step size and the step width and (2) a location of the center of mass; and
determining whether the center of mass is aligned within the base of support.

5. The system as claimed in claim 4, wherein the controller is further configured to:
from the signals, determine a velocity of the center of mass and whether the center of mass is within the base of support; and
determining the risk of falling in response to one of:
the center of mass being outside the base of support and having a velocity which is insufficient to bring the center of mass back within the base of support, or
the center of mass is within the base of support and the velocity is outwards from the base of support.

6. The system as claimed in claim 1, wherein the controller is further configured to:
from the signals, determine a velocity of the center of mass and whether the center of mass is within the base of support; and
determining the risk of falling in response to one of:
the center of mass being outside the base of support and having a velocity which is insufficient to bring the center of mass back within the base of support, and
the center of mass is within the base of support and the velocity is outwards from the base of support.

7. The system as claimed in claim 1, wherein the one or more sensors include accelerometers, and the trajectories are estimated by integrating the signals from the accelerometers.

8. The system as claimed in claim 1, wherein the one or more sensors include accelerometers, and the controller is configured to estimate the trajectory of the center of mass of the user relative to the trajectory of the base of support of the body by computing one of a Lyapunov exponent and a Floquet Multiplier from the movement signals.

9. A system for fall prevention for a user comprising:
one or more sensors configured for attachment to respective portions of a body of the user, the sensors being configured to measure movement of the respective portions of the body and to translate the measured movement into movement signals; and
a controller configured to:
receive the movement signals,
estimate a trajectory of a center of mass of the user from the movement signals,
estimate a trajectory of a base of support of the body from the movement signals, the base of support of the user being a surface defined by a step width and a step length of the user when walking,
determine a difference between the estimated trajectories of the center of mass of the user and of the base of support of the body of the user, and
determine a risk of falling from the difference between the trajectories.

10. The system as claimed in claim 9, wherein the control unit is further configured to cause an alarm signal to be generated based on the determined risk of fall to alert the user or a caregiver.

11. The system as claimed in claim 9, wherein the one or more sensors include a first accelerometer configured for attachment to an upper portion of the user's body for measuring movement of the upper portion of the body, and the controller is configured to estimate the trajectory of the center of mass of the user from the signals from the first accelerometer.

12. The system as claimed in claim 11, wherein the controller is further configured to estimate the trajectory of the base of support of the body using the signals from the first accelerometer.

13. The system as claimed in claim 11, wherein the system comprises at least one second accelerometer configured for attachment to a lower portion of the users body to output signals representing movement of the base of support of the body during walking, and the controller is further configured to estimate a trajectory of the base of support from the second accelerometer output signals.

14. The system as claimed in claim 11, wherein the one or more sensors include another accelerometer configured for attachment to a lower portion of the user's body and wherein the controller is further configured to:
from the signals from another accelerometer, determine the step length and the step width of the user when walking and a location of the base of support;
from the signals from the first accelerometer, determine a velocity and location of the center of mass of the user; and determining the risk of falling in response to one of:
- the center of mass being outside the base of support and having a velocity which is insufficient to bring the center of mass back within the base of support, and
- the center of mass is within the base of support and the velocity is outwards from the base of support.

15. A method for fall prevention for a user comprising, with a controller:
- receiving movement signals measured by one or more sensors configured for attachment to respective portions of a body of the user and for measuring movement of the respective portions of the body and translating the measured movement into the movement signals;
- estimating a trajectory of a center of mass of the user from the movement signals;
- estimating a trajectory of a base of support of the body from the movement signals, the base of support of the user being a surface defined by a step width and a step length of the user when walking;
- determining a difference between the estimated trajectories of the center of mass of the user and the base of support of the body; and
- determining a risk of falling from the difference between the trajectories.

16. A non-transitory computer-readable medium carrying instructions for controlling a processor controller to perform the method as claimed in claim 15.

17. The method as claimed in claim 15, further including, with the controller:
- from the movement signals, determining a velocity of the center of mass and whether the center of mass is within the base of support;
- determining the falling risk based on one of:
  - the center of mass being outside the base of support and having a velocity which is insufficient to bring the center of mass back within the base of support, and
  - the center of mass is within the base of support and the velocity is outwards from the base of support.

18. The method as claimed in claim 15, further including, with the controller:
- determining whether the movement signals have a reoccurring pattern over time in a multi-dimensional space;
- based on the periodicity of the reoccurring pattern, determining whether the user is in a walking steady state;
- detecting peaks in the motion signals to delineate individual steps;
- determining the step length and the step width; and
- determining whether the center of mass is aligned within the base of support.

* * * * *